(12) United States Patent
Haendler et al.

(10) Patent No.: US 8,129,138 B2
(45) Date of Patent: Mar. 6, 2012

(54) METHOD AND APPARATUS FOR DETERMINING AN ANALYTE IN A LIQUID SAMPLE

(75) Inventors: Erich Haendler, Lampertheim (DE); Norbert Oranth, Hirschberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 391 days.

(21) Appl. No.: 12/478,878

(22) Filed: Jun. 5, 2009

(65) Prior Publication Data

US 2009/0305332 A1   Dec. 10, 2009

(30) Foreign Application Priority Data

Jun. 5, 2008   (EP) .................................... 08010289

(51) Int. Cl.
*C12M 1/34* (2006.01)
*C12Q 1/02* (2006.01)
*G01N 21/00* (2006.01)
*G01N 30/96* (2006.01)

(52) U.S. Cl. ....... 435/29; 204/403.01; 422/69; 436/164; 435/287.1

(58) Field of Classification Search .................... 435/29, 435/287.1; 422/69; 204/403.01; 702/118
See application file for complete search history.

(56) References Cited

U.S. PATENT DOCUMENTS

| | | | |
|---|---|---|---|
| 5,723,345 | A | 3/1998 | Yamauchi et al. |
| 7,338,639 | B2 * | 3/2008 | Burke et al. ............... 422/82.01 |
| 7,550,069 | B2 * | 6/2009 | Feldman et al. ......... 204/403.14 |
| 2006/0155501 | A1 * | 7/2006 | Hempel ........................ 702/118 |

OTHER PUBLICATIONS

Holbrook, et al., "Protein Fluorescence of Lactate Dehydrogenase", Biochemical Journal, 128:921-931 (1972).

Schult, et al., "Disposable Optical Sensor Chip for medical Diagnostics: New Ways in Bioanalysis", Analytical Chemistry, 71:5430-5435 (1999).

Hanen, "Principles and Applications of Flow Injection Analysis in Biosensors", Journal of Molecular Recognition, 9:216-325 (1996).

\* cited by examiner

*Primary Examiner* — Herbert J Lilling
(74) *Attorney, Agent, or Firm* — McDonnell Boehnen Hulbert & Berghoff LLP.

(57) ABSTRACT

A method for the determination of an analyte in a liquid sample, especially a body liquid sample, with the aid of an analytical apparatus. The apparatus receives a first measuring signal $s_i$ ($i=0, 1, \ldots$) and a second measuring signal $s_j$ ($j=1, 2, \ldots; j>i$) for a test system with several successively arranged measuring areas through which a liquid sample with an analyte can flow after being applied on the test system are received by an evaluation apparatus comprised by the analytical apparatus, wherein the first measuring signal $s_i$ indicates a part of the analyte bound in a first measuring area and the second measuring signal $s_j$ indicates a part of the analyte bound in a second measuring area that is arranged downstream the first measuring area on the test system after the application of the liquid sample on the test system, a concentration measure N correlating with the concentration of the analyte in the liquid sample is determined by the evaluation apparatus in accordance with the following linkage of measuring signals:

$$N = \frac{(s_j)^{i+2}}{\left[s_i - ((s_i)^{j-i-1} \cdot s_j)^{\frac{1}{j-i}}\right] \cdot ((s_i)^{j-i-1} \cdot s_j)^{\frac{i}{j-i}}}, \text{ and}$$

the concentration measurement is outputted by the evaluation apparatus after a selective further processing. Furthermore, the invention relates to an analytical apparatus for the determination of an analyte in a liquid sample as well as to a computer readable medium for performing function to determine an analyte in a liquid sample.

10 Claims, 1 Drawing Sheet

METHOD AND APPARATUS FOR DETERMINING AN ANALYTE IN A LIQUID SAMPLE

CROSS REFERENCE TO RELATED APPLICATION

This application claims the benefit of European Patent Application No. EP 08 010 289.0 filed on Jun. 5, 2008.

BACKGROUND OF THE INVENTION

1. Field of the Invention

The invention relates to a method for the determination of an analyte in a liquid sample, especially a body liquid sample, as well as to an analytical apparatus and a computer program product.

2. Description of Related Art

As a supplement or an alternative, the determination of an analyte in the liquid sample can also comprise, in addition to the basic detection of the analyte itself, the measuring of analyte-specific properties in the liquid sample. Here, the liquid sample to be examined is customarily applied on a test system or test element with several analyte detection zones that are also designated as measuring- or examination areas. For example, the applied liquid sample moves here along a straight line on which the several measuring areas or detection zones are arranged. Analyte-specific catch structures are arranged in the measuring areas that can have a circular, rectangular or linear form, so that a part of the analyte from the liquid sample is bound in the measuring areas.

The analyte or analytes is/are customarily labeled directly or via antibodies and as a result are prepared for a subsequent optical evaluation of the test system. A preparation of the test system or test element can optionally comprise the cleaning or washing with a puffer solution, diluting solution or a wash solution. Finally, the test system, that is, for example, a dry chemical test element, can then be evaluated by optical sampling in order in particular to determine the occurrence of one or more certain analytes in the measuring areas.

In the optical sampling, which is also designated as optical scanning, measuring light beams produced in the scanned examination areas are detected with a detector apparatus after leaving the examination areas. The measuring light beams can be produced by radiating test light beams produced for their part by a suitable monochromatic or polychromatic light source onto the measuring areas charged with optically active substances to be measured. In the measuring areas the light of the test light beams then interacts with the optically active substances so that a corresponding change of the optical properties of the test light beams results that then leave the measuring area as measured light beams. During the radiating in of test light the absorption, the transmission, the reflection or also the fluorescence can be examined as optical properties of the measuring light beams. Furthermore, measuring light beams can be based on a luminescence of the optically active substances in the measuring areas.

During the optical sampling of the test element/test system, for example, the test element and the detector apparatus which detects the measuring light beams or the test element and the light source can be shifted relative to one another in order to optically analyze measuring area after measuring area in this manner.

The measuring areas are optically examined with the aid of optical measuring methods such as absorption, fluorescence, transmission or reflection in order to analyze the binding of the analytes in a particular zone. Here the so-called test light beams are put on the measuring area that then interact in the measuring area with optical labels that bind to the analyte-specific catch structures, as a result of which the measuring light beams are produced, that are detected with the aid of an optical detector apparatus. For example, a photodiode or a photodiode arrangement can serve as such optical detector apparatuses. The signals measured for the measuring light beams are used in order to determine, for example, a concentration or other properties of the analyte in the liquid sample.

The detected measuring light beams are customarily dependent on the binding efficiency with which a complex of the analyte flowing past the measuring area or the detection zone binds there to the catch structures. The binding efficiency is for its part generally dependent on different properties such as the type of the substrate (membrane) used for the measuring area, the individual liquid sample, the analyte-specific catch structures or the temperature. The binding efficiency is therefore very different for different measuring- or analytical situations. This means that a variation of the binding efficiency usually directly affects the result of analysis.

SUMMARY OF THE INVENTION

The invention is directed to a method for the determination of an analyte in a liquid sample, especially a body liquid sample, with the aid of an analytical apparatus in which a first measuring signal $s_i$ ($i=0, 1, \ldots$) and a second measuring signal $s_j$ ($j=1, 2, \ldots$; $j>i$) for a test system with several successively arranged measuring areas through which a liquid sample with an analyte can flow after being applied on the test system are received by an evaluation apparatus comprised by the analytical apparatus, wherein the first measuring signal $s_i$ indicates a part of the analyte bound in a first measuring area and the second measuring signal $s_j$ indicates a part of the analyte bound in a second measuring area that is arranged downstream the first measuring area on the test system after the application of the liquid sample on the test system, a concentration measure N correlating with the concentration of the analyte in the liquid sample is determined by the evaluation apparatus in accordance with the following linkage of measuring signals:

$$N = \frac{(s_j)^{i+2}}{\left[s_i - ((s_i)^{j-i-1} \cdot s_j)^{\frac{1}{j-i}}\right] \cdot ((s_i)^{j-i-1} \cdot s_j)^{\frac{i}{j-i}}}, \text{ and}$$

the concentration measure N is outputted by the evaluation apparatus after a selective further processing.

In various aspects of the invention, the first measuring area is an ith measuring area and the second measuring area is a jth measuring area.

According to a further aspect of the invention an analytical apparatus for the determination of an analyte in a liquid sample, especially a body liquid sample, is created with an evaluation apparatus that is configured to receive a first measuring signal $s_i$ ($i=0, 1, \ldots$) and a second measuring signal $s_j$ ($j=1, 2, \ldots$; $j>i$) for a test system with several successively arranged measuring areas through which a liquid sample with an analyte can flow after being applied on the test system, wherein the first measuring signal $s_i$ indicates a part of the analyte bound in a first measuring area and the second measuring signal $s_j$ indicates a part of the analyte bound in a second measuring area that is arranged downstream the first measuring area on the test system after the application of the liquid sample on the test system, and wherein the evaluation apparatus is furthermore configured for determining and outputting a concentration measure N correlating with the concentration of the analyte in the liquid sample in accordance with the following linkage of measuring signals:

$$N = \frac{(s_j)^{i+2}}{\left[s_i - ((s_i)^{j-i-1} \cdot s_j)^{\frac{1}{j-i}}\right] \cdot ((s_i)^{j-i-1} \cdot s_j)^{\frac{i}{j-i}}}.$$

DETAILED DESCRIPTION

Figure 1:
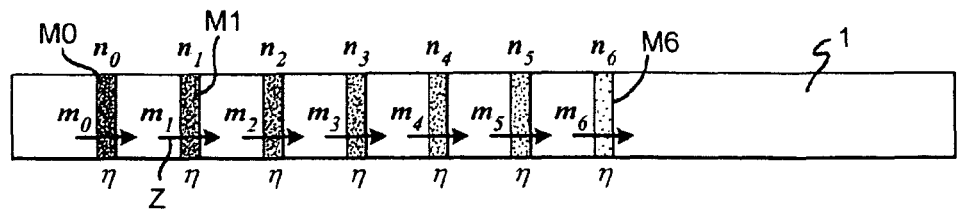
FIG. 1 is schematic view of the test system with several measuring areas extending transversally to a direction of spread of a liquid sample on the test system.

An essential advantage achieved with the invention over the state of the art is that the determination of the concentration measure by the evaluation apparatus is independent of the binding efficiency for the analyte of the liquid sample in the measuring areas of the test system. The suggested signal processing eliminates so to say the influence of the binding efficiency. In this manner the determination of the concentration measure for the analyte in the liquid sample is far less dependent on the analytical conditions that frequently change from situation to situation.

In the sense understood here the concentration measure N correlates with the concentration in such a manner that an increase of the concentration also brings about an increase of the concentration measure. The same applies to a decrease of the concentration measure at a decrease of the concentration. The correlation can be of a linear or of a non-linear nature. A functional connection between concentration and concentration measure does not have to be known in a mathematically exact form here but rather the actual concentration can also be determined using an experimentally determined gauging or calibration curve.

The suggested technology for the determination of analytes is furthermore distinguished in that in order to evaluate the analysis based on the test system, measuring signals for any measuring areas of the test system can be used. The measuring signals themselves can be detected in a known manner with the aid of a suitable detector apparatus like those known as such in various embodiments. There is the possibility here of integrating the evaluation apparatus together with the detector apparatus in the analytical apparatus. Even a construction of the evaluation apparatus separately from the detector apparatus can be provided, wherein the evaluation apparatus receives the measuring signals in electronic form from the detector apparatus directly or via an intermediate storage of the electronic signals.

In a preferred embodiment measuring signals are used for a test system in order to determine the concentration measure in which the measuring areas extend transversally to the direction of flow of the liquid sample on the test system. Measuring signals can be evaluated for measuring areas with different forms, for example, of measuring areas that have a rectangular, circular or linear form.

The use of the suggested technologies in conjunction with the determining of at least one analyte in a body liquid sample such as a blood sample or urine sample is especially suitable.

The concentration measure proportional to the concentration of the analyte in the liquid sample can be selectively further processed with the aid of the evaluation apparatus in order to determine an actual concentration of the analyte as absolute or relative magnitude. In this connection, for example, a further processing of the concentration measure can take place using comparison signals detected previously in the framework of a calibration or gauging. The independence of the concentration measure from the binding efficiency of the analyte in the measuring areas or detection zones leads to the independence of an optionally determined actual concentration from the binding efficiency.

A preferred further development of the invention provides that a first optical measuring signal is received as the first measuring signal and a second optical measuring signal is received as the second measuring signal. The first and the second optical signals can be formed, according to a signal type, selected from the following group of signal types: fluorescence signal, transmission signal, absorption signal and reflection signal.

An advantageous embodiment of the invention can provide that the first and the second measuring area are adjacent areas on the test system, so that $j=i+1$, and the concentration measure N is determined by the evaluation apparatus in accordance with the following simplified linking of measuring signals:

$$N = \frac{(s_i)^{i+2}}{[s_i - s_{i+1}] \cdot (s_{i+1})^i}.$$

In conjunction with the advantageous embodiments of the analytical apparatus for the determination of an analyte in a liquid sample, the explanations made in connection with the previously described embodiments of the method apply in a corresponding manner. Furthermore, a detector apparatus can be provided with the analytical apparatus which detector apparatus is configured to detect the first and the second measuring signal and to output them to the evaluation apparatus. In a preferred further development of the invention the detector apparatus is an optical detector apparatus that is configured to detect in an appropriate manner the first and the second optical measuring signal of a signal type selected from the following group of signal types: fluorescence signal, transmission signal, absorption signal and reflection signal.

A test system can be integrated in the analytical apparatus in an advantageous embodiment of the invention which test system is preferably configured to be replaceable or for multiple use. Independently of whether the test system is integrated in the analytical apparatus or is formed separately from it, the test system can be a detection system with measuring areas formed separately from each other or with a cohesive measuring area that can be utilized in such a manner with measuring technology that successively arranged partial measuring areas can be utilized for the detection of the measuring signals. The technologies suggested here for the determination of the concentration measure can be used for both types of test systems.

A further development of the invention can provide using the concentration measure determined using the first and the second measuring signal together with the result of further such analyses, in which at least one measuring signal for a further measuring area is included, for example, in the sense of a formation of mean value or average value. In this manner measuring signals are used for more than two measuring areas of the test system FIG. 1 shows a schematic view of a test system 1 on which several measuring areas or detection zones M0, ..., M6 are formed along a direction of spread 2 and extending transversally to it. A liquid sample, especially a body liquid sample, that contains one or more analytes to be detected can be placed on the test system 1. The one or more analyte(s) is/are marked with a so-called label. Then, analyte-specific catch structures to which the analyte binds are formed in the measuring areas M0, ..., M6. The markings or labels of the bound analyte complexes can then be evaluated with measuring technology for the measuring areas M0, ..., M6, preferably with the aid of an optical evaluation in the form of absorption-, fluorescent-, transmission- or reflection light. For this, test light beams are radiated onto the measuring areas M0, ..., M6 and associated measuring light beams optically detected with the aid of a detector apparatus (not shown).

The different degree of shading of the measuring areas M0, ..., M6 in FIG. 1 shows the different range in which the analyte is bound in the measuring areas M0, ..., M6. The binding takes place to the greatest extent in the measuring area M0, in contrast to which in the last-shown measuring area M6 only a small amount of the analyte is present in the liquid sample, for which reason only few analyte molecules or analyte structures are bound there.

Let $s_i$ (i=0, 1, ..., 6 ) be the measuring signal detected for the measuring area M0, ..., M6, that is, in particular an optical measuring signal that indicates the extent or the range of the binding of analyte structures in the measuring area. To this end it is preferred in an embodiment to use measuring signals for measuring areas in which a start can be made from a proportionality between the number of the bound, marked analyte structures and the intensity of the measuring signal. The latter can potentially not be the case, for example, especially in the first measuring areas after the application region of the test system 1, since a falsification of measuring value can occur there on account of the high number of the bound, marked analyte structures. The high density of labels can result in non-linear optical behavior.

Furthermore, measuring signals are preferably used in a purposeful manner that are located in the dynamic range of the detector apparatus, that is, the range in which the response function of the detector that is relevant according to measuring technology behaves in a linear manner.

Furthermore, let $\eta$ be the probability (binding efficiency) (independent of i) with which a marked analyte moving over one of the measuring areas is bound in it, that is, the following is valid:

$$n_i = \eta \cdot m_i \quad i=0, 1, 2, \ldots, \tag{1}$$

$m_i$ is the number of the labels moving over the i-th measuring area.

The detection system preferably constructed as optical detector apparatus then furnishes measuring signals $s_i$ during the measuring of the measuring areas that are proportional to the number of the labels trapped in the particular measuring area, that is, to the number of the analyte elements marked and bound with a label. The following is valid:

$$s_i = C \cdot n_i \quad i=0, 1, 2, \ldots, \tag{2}$$

in which C is a proportionality factor.

The measuring signals $s_i$ detected in this manner for the measuring areas are then processed with the aid of an evaluation apparatus (not shown), which is, for example, a microprocessor unit configured in accordance with hardware and/or software technology, in accordance with the following signal linking:

$$N_i = \frac{(s_i)^{i+2}}{(s_i - s_{i+1}) \cdot (s_{i+1})^i} \tag{3}$$

$$i = 0, 1, 2, \ldots$$

The detected measure $N_i$ is proportional to $m_0$, that is, to the number of the label structures that reach the first measuring area M0 and is no longer dependent on the binding efficiency $\eta$.

This is explained in detail in the following. The following is valid:

$$m_i = (m_0) \cdot (1-\eta)^i \quad i=0, 1, 2, \tag{4}$$

This yields $n_i = m_{i+1} - m_i = m_0 \cdot (1-\eta)^{i+1} - m_0 \cdot (1-\eta)^i$ to:

$$n_i = m_0 \cdot \eta \cdot (1-\eta)^i \tag{5}$$

Equation (5) inserted in equation (3) yields:

$$N_i = \frac{(C \cdot m_0 \cdot \eta \cdot (1-\eta)^i)^{i+2}}{(C \cdot m_0 \cdot \eta \cdot (1-\eta)^i - C \cdot m_0 \cdot \eta \cdot (1-\eta)^{i+1}) \cdot (C \cdot m_0 \cdot \eta \cdot (1-\eta)^{i+1})^i} \tag{6}$$

This can be simplified to:

$$N_i = C \cdot m_0 \quad i=0, 1, 2, \tag{7}$$

The linking of measuring signals according to equation (3) refers to the evaluation of adjacent measuring areas of the test system 1.

A measuring signal evaluation leading to an equal advantage, namely, the independence of the binding efficiency $\eta$, can now also be indicated for non-adjacent measuring areas of the test system 1, wherein in the following without limitation of the generality the proportionality factor is set to C=1:

Case 1: $j-i=1$ $\eta=1-\frac{n_j}{n_i}$ $N_i = m_0 = \left[\frac{s_i^{i+2}}{(s_j)^i \cdot (s_i - s_j)}\right]$ Case 2: $j-i=2$ $\eta=1-\left(\frac{n_j}{n_i}\right)^{\frac{1}{2}}$ $N_i = m_0 = \frac{s_i^{i+2}}{\left[s_i - (s_i \cdot s_j)^{\frac{1}{2}}\right] \cdot (s_i \cdot s_j)^{\frac{i}{2}}}$ Case 3: $j-i=3$ $\eta=1-\left(\frac{n_j}{n_i}\right)^{\frac{1}{3}}$ $N_i = m_0 = \frac{s_i^{i+2}}{\left[s_i - (s_i^2 \cdot s_j)^{\frac{1}{3}}\right] \cdot (s_i^2 \cdot s_j)^{\frac{i}{3}}}$ Case 4: $j-i=4$ $\eta=1-\left(\frac{n_j}{n_i}\right)^{\frac{1}{4}}$ $N_i = m_0 = \frac{s_i^{i+2}}{\left[s_i - (s_i^3 \cdot s_j)^{\frac{1}{4}}\right] \cdot (s_i^3 \cdot s_j)^{\frac{i}{4}}}$ Case 5: $j-i=5$ $\eta=1-\left(\frac{n_j}{n_i}\right)^{\frac{1}{5}}$ $N_i = m_0 = \frac{s_i^{i+2}}{\left[s_i - (s_i^4 \cdot s_j)^{\frac{1}{5}}\right] \cdot (s_i^4 \cdot s_j)^{\frac{i}{5}}}$ Case 1 refers once again to adjacent measuring areas for the comparison, thus j=i+1.

The following linking of measuring signals now results in generalized form from the preceding explanations:

$$N_{ij} = \frac{(s_j)^{i+2}}{\left[s_i - ((s_i)^{j-i-1} \cdot s_j)^{\frac{1}{j-i}}\right] \cdot ((s_i)^{j-i-1} \cdot s_j)^{\frac{i}{j-i}}},$$

that shows a linking of measuring signals for any measuring areas of the test system 1, that allows the determination of the concentration measure $N_{ij}$ independently of the binding efficiency $\eta$.

The advantage of using $N_i$ or $N_{ij}$ as measure for the analyte concentration can be further examined using the following considerations. If the effect of a variation of the binding efficiency $\eta$ is observed according to the law of error propagation, a comparative observation with other linkings of measuring signals shows:

in the optimal working range of the detector, thus, advantageously the linear working range. Inversely, very low concentrations would be determined from the measuring signals of the last two measuring areas.

Figure 3:
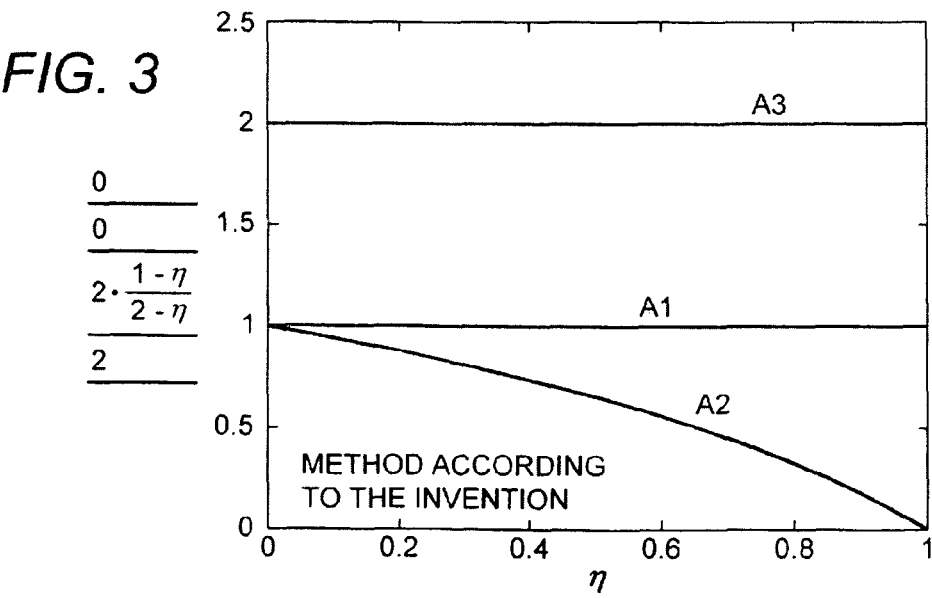
FIG. 3 shows a plot for an error propagation.

The dynamic expansion associated therewith is visualized in FIG. 3. The drop of the number of the bound labels (respectively of the measuring signal) according to equation (5) with rising ordinal number of the measuring area for different values of $\eta$ is shown. It can be gathered from the plot in FIG. 3 that the dynamics of the detection can be increased by 2.5 orders of magnitude with five measuring areas at a binding efficiency of $\eta=0.8$.

The described features of the invention disclosed in the previous description, the claims and the drawings can be significant individually as well as in any combination for the realization of the invention in its different embodiments.

| Variant | Linking rule | Error propagation upon variation of $\eta$ |
|---|---|---|
| Suggested processing of measuring signals | $N_i = \dfrac{s_i(\eta)^{i+2}}{(s_i(\eta) - s_{i+1}(\eta)) \cdot s_{i+1}(\eta)^1}$ | $\dfrac{dN_i}{N_i} = 0 \cdot \dfrac{d\eta}{\eta}$ |
| Evaluation of only one measuring area- A1 | $N_i^{A1} = s_i(\eta)$ | $\dfrac{dN_i^{A1}}{N_i^{A1}} = \dfrac{1 - \eta(i+1)}{1 - \eta} \cdot \dfrac{d\eta}{\eta}$ <br><br> For i = 0 the following results: <br><br> $\dfrac{dN_0^{A1}}{N_0^{A1}} = 1 \cdot \dfrac{d\eta}{\eta}$ |
| Additive linking of the measuring signals for adjacent measuring areas- A2 | $N_i^{A2} = s_i(\eta) + s_{i+1}(\eta)$ | $\dfrac{dN_i^{A2}}{N_i^{A2}} = \dfrac{\eta \cdot (\eta - 2) \cdot (i+2) + 2}{(\eta - 2) \cdot (\eta - 1)} \cdot \dfrac{d\eta}{\eta}$ <br><br> For i = 0 the following results: <br><br> $\dfrac{dN_0^{A2}}{N_0^{A2}} = 2 \cdot \dfrac{1 - \eta}{2 - \eta} \cdot \dfrac{d\eta}{\eta}$ |
| Subtraction linking of the measuring signals for adjacent measuring areas- A3 | $N_i^{A3} = s_i(\eta) - s_{i+1}(\eta)$ | $\dfrac{dN_i^{A3}}{N_i^{A3}} = \left(2 - \dfrac{i \cdot \eta}{(1 - \eta)}\right) \cdot \dfrac{d\eta}{\eta}$ <br><br> For i = 0 the following results: <br><br> $\dfrac{dN_0^{A3}}{N_0^{A3}} = 2 \cdot \dfrac{d\eta}{\eta}$ |

Figure 2:
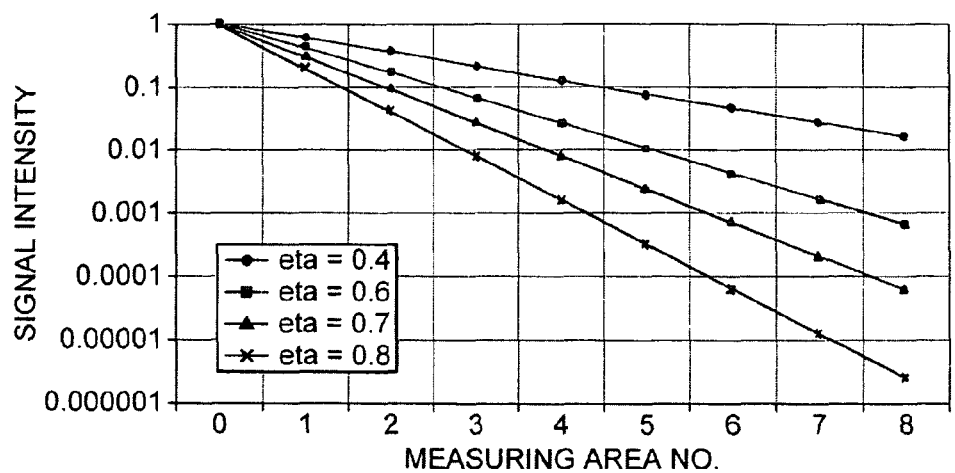
FIG. 2 shows a plot for a signal drop in the case of several successively located measuring areas or detection zones with a linear form.

FIG. 2 is a graphic view for an error propagation visualizing the different error propagations for the case i=0.

Further it emerges from the facts that the measuring signals in the measuring of the detection zone become all the smaller the further to the rear (viewed in the direction of flow/spread) the particular detection zone is located. The preferably optically executed detection can be adjusted so that in the case of very high analyte concentrations the number of the label measuring area $n_0$ is so high that the detection system is in the limitation at these measuring areas, thus, a saturation of the detector occurs. In this case $N_i$ would be determined from the measuring signals for two detection zones or measuring areas at which the measuring signal had dropped so far that it falls

What is claimed is:

1. A method for the determination of an analyte in a liquid sample with the aid of an analytical apparatus, the method comprising
   (a) applying a liquid sample to a test system comprising several successively arranged measuring areas, and through which liquid sample can flow;
   (b) measuring a first measuring signal $s_i$ and a second measuring signal $s_j$ wherein the first measuring signal $s_i$ indicates a part of the analyte bound in a ith measuring area and the second measuring signal $s_j$ indicates a part of the analyte bound in a jth measuring area that is arranged downstream the ith measuring area on the test system, (c) calculating a concentration measure N correlating with the concentration of the analyte in the liquid sample is determined by the analytical apparatus in accordance with the following linkage of measuring signals:

$$N = \frac{(s_j)^{i+2}}{\left[s_i - ((s_i)^{j-i-1} \cdot s_j)^{\frac{1}{j-i}}\right] \cdot ((s_i)^{j-i-1} \cdot s_j)^{\frac{i}{j-i}}}.$$

2. The method of claim 1, wherein the first measuring signal is an optical signal and the second measuring signal is an optical signal.

3. The method of claim 1, wherein the ith and the jth measuring areas are adjacent areas on the test system, so that j=i+1, and the concentration measure N is determined by the analytical apparatus in accordance with the following formula:

$$N = \frac{(s_i)^{i+2}}{[s_i - s_{i+1}] \cdot (s_{i+1})^i}.$$

4. An analytical apparatus for the determination of an analyte in a liquid sample, the apparatus being configured to receive a first measuring signal $s_i$ and a second measuring signal $s_j$ from a test system with several successively arranged measuring areas through which the liquid sample can flow after being applied on the test system, t, wherein the first measuring signal $s_i$ indicates a part of the analyte bound in a ith measuring area and the second measuring signal $s_j$ indicates a part of the analyte bound in a jth measuring area that is arranged downstream the jth measuring area, and wherein analytical apparatus further comprises an evaluation apparatus configured for determining and outputting a concentration measure N correlating with the concentration of the analyte in the liquid sample in accordance with the following formula:

$$N = \frac{(s_j)^{i+2}}{\left[s_i - ((s_i)^{j-i-1} \cdot s_j)^{\frac{1}{j-i}}\right] \cdot ((s_i)^{j-i-1} \cdot s_j)^{\frac{i}{j-i}}}.$$

5. The analytical apparatus of claim 4, wherein the evaluation apparatus is further configured to receive a first optical signal as the first measuring signal and a second optical signal as the second measuring signal.

6. The analytical apparatus of claim 4, wherein the evaluation apparatus is further configured to determine the concentration measure N in accordance with the following formula:

$$N = \frac{(s_i)^{i+2}}{[s_i - s_{i+1}] \cdot (s_{i+1})^i},$$

when the ith and the jth measuring areas are adjacent areas on the test system, so that j=i+1.

7. The apparatus of claim 4, further comprising a detector apparatus for detecting the first and the second measuring signal and to output them to the evaluation apparatus.

8. The apparatus of claim 5, further comprising a detector apparatus that detects the first and the second optical measuring signals; wherein the measuring signals are independently selected from the following group of signal types: fluorescence signal, transmission signal, absorption signal and reflection signal.

9. The analytical apparatus of claim 4, wherein the analytical apparatus is a test system.

10. A computer readable medium encoded with a computer program that enables an evaluation apparatus to perform functions comprising:

receiving a first measuring signal $s_i$ and a second measuring signal $s_j$ for a test system with several successively arranged measuring areas through which a liquid sample with an analyte can flow after being applied on the test system, wherein the ith measuring signal $s_i$ indicates a part of the analyte bound in a first measuring area and the second measuring signal $s_j$ indicates a part of the analyte bound in jth measuring area that is arranged downstream the ith measuring area on the test system after the application of the liquid sample on the test system, determining a concentration measure N correlating with the concentration of the analyte in the liquid sample in accordance with the following formula:

$$N = \frac{(s_j)^{i+2}}{\left[s_i - ((s_i)^{j-i-1} \cdot s_j)^{\frac{1}{j-i}}\right] \cdot ((s_i)^{j-i-1} \cdot s_j)^{\frac{i}{j-i}}}, \text{ and}$$

outputting the concentration measure N.

* * * * *